(12) United States Patent
Kitagawa et al.

(10) Patent No.: US 9,791,376 B2
(45) Date of Patent: Oct. 17, 2017

(54) OPTICAL SENSOR

(71) Applicant: Panasonic Intellectual Property Management Co., Ltd., Osaka (JP)

(72) Inventors: Yusuke Kitagawa, Kyoto (JP); Kiyoshi Hashimotodani, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 57 days.

(21) Appl. No.: 14/404,491

(22) PCT Filed: Jun. 6, 2013

(86) PCT No.: PCT/JP2013/003556
§ 371 (c)(1),
(2) Date: Nov. 28, 2014

(87) PCT Pub. No.: WO2013/187022
PCT Pub. Date: Dec. 19, 2013

(65) Prior Publication Data
US 2015/0110675 A1    Apr. 23, 2015

(30) Foreign Application Priority Data

Jun. 12, 2012    (JP) ................. 2012-132462

(51) Int. Cl.
*G01N 21/75*    (2006.01)
*G01N 21/25*    (2006.01)
*G01N 21/78*    (2006.01)

(52) U.S. Cl.
CPC ............ *G01N 21/75* (2013.01); *G01N 21/25* (2013.01); *G01N 21/78* (2013.01); *G01N 2021/752* (2013.01); *G01N 2021/757* (2013.01)

(58) Field of Classification Search
CPC ............ G01N 21/75; G01N 2021/752; G01N 2021/757; G01N 27/3278
(Continued)

(56) References Cited

U.S. PATENT DOCUMENTS 5,208,163 A * 5/1993 Charlton ........... B01L 3/502753
422/947
6,221,625 B1 * 4/2001 Ashihara ............. G01N 33/542
422/424
(Continued)

FOREIGN PATENT DOCUMENTS

JP    2004-317489    11/2004
JP    2006-184010    7/2006
(Continued)

OTHER PUBLICATIONS

International Search Report of PCT application No. PCT/JP2013/003556 dated Jul. 9, 2013.

*Primary Examiner* — Jill Warden
*Assistant Examiner* — Jacqueline Brazin
(74) *Attorney, Agent, or Firm* — McDermott Will & Emery LLP (57) ABSTRACT

An optical sensor includes an input part, a fixing part, and a determining part. The input part is provided on the upper side of the sensor. The fixing part on which a carrier is disposed is provided below the input part. The carrier has an acceptor that reacts with an analyte contained in the sample and is fixed on the carrier. The determining part includes a first metal layer, a second metal layer, and a hollow area. The first metal layer is configured to receive an electromagnetic wave. The second metal layer faces the first metal layer. The hollow area is sandwiched between the first metal layer and the second metal layer. The input part, the fixing part, and (Continued)

the hollow area form a part of a passage where the sample flows from the input part to the hollow area.

23 Claims, 9 Drawing Sheets

(58) Field of Classification Search
USPC .................................................... 422/82.05
See application file for complete search history.

(56) References Cited

U.S. PATENT DOCUMENTS

| | | | |
|---|---|---|---|
| 6,245,296 B1* | 6/2001 | Ligler et al. .................. 422/402 |
| 2004/0166551 A1* | 8/2004 | Moulds ................. B01L 3/5021 |
| | | | 435/13 |
| 2010/0045993 A1 | 2/2010 | Martini et al. |
| 2010/0311186 A1* | 12/2010 | Gregory ..................... B03C 1/01 |
| | | | 436/501 |
| 2010/0330698 A1* | 12/2010 | Evers ............................ 436/501 |
| 2012/0028247 A1* | 2/2012 | Tamura ................ G01N 21/553 |
| | | | 435/5 |

FOREIGN PATENT DOCUMENTS

| | | | |
|---|---|---|---|
| JP | 2006184010 | * | 7/2006 |
| JP | 2010-048807 | | 3/2010 |
| WO | 2010/122776 | | 10/2010 |

* cited by examiner

OPTICAL SENSOR

TECHNICAL FIELD

The present invention relates to optical sensors that can be used typically for detecting viruses or the like.

BACKGROUND ART

Figure 9:
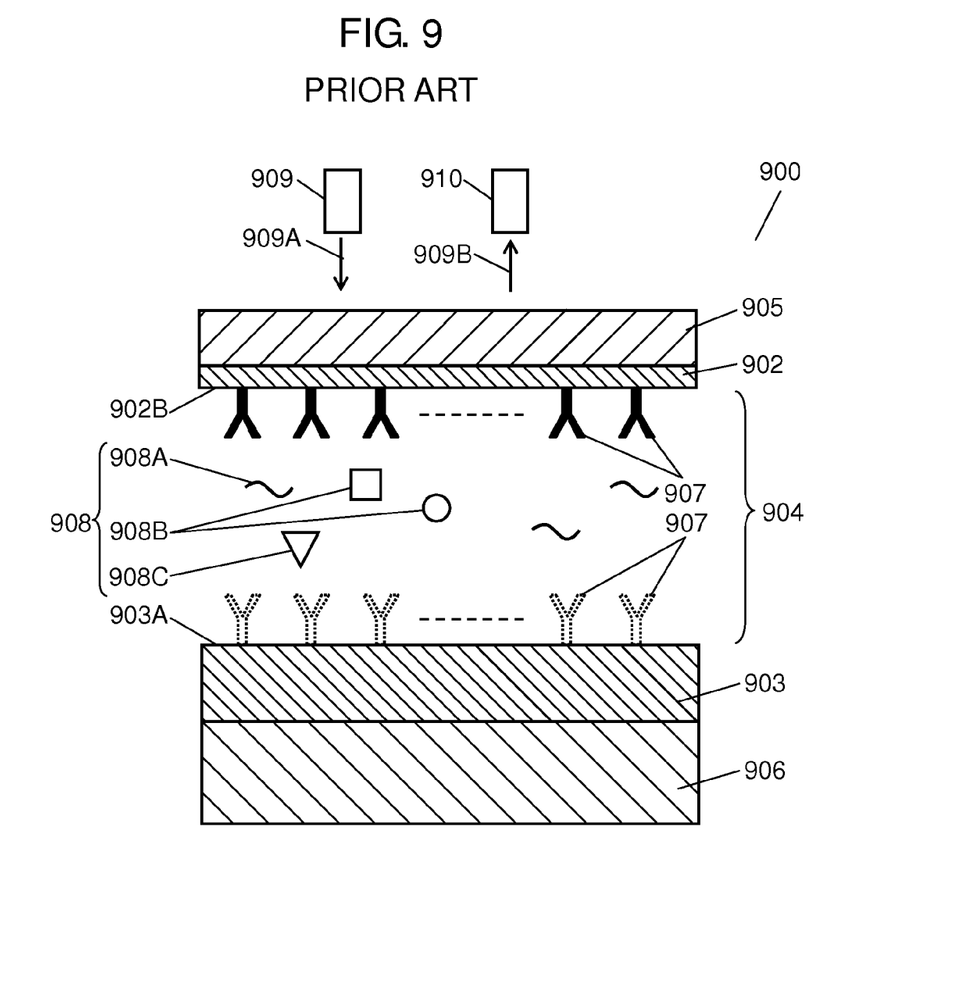
FIG. 9 is a sectional view of a conventional optical sensor.

FIG. 9 is a sectional view of optical sensor 900 that can be used typically for detecting viruses (e.g., PTL1). Optical sensor 900 includes first metal layer 902 and second metal layer 903. A bottom face of first metal layer 902 faces a top face of second metal layer 903. First metal layer 902 is fixed to supporting part 905, and second metal layer 903 is fixed to supporting part 906 to retain their shapes. The thickness of first metal layer 902 is in a range from 30 nm to 45 nm. The thickness of second metal layer 903 is 100 nm or more.

Hollow area 904 is provided between first metal layer 902 and second metal layer 903. Hollow area 904 is configured to be filled with sample 908 including solvent 908A, non-specific specimen 908B, and a substance to be detected (i.e. analyte) 908C. Acceptors 907 are physically adsorbed on at least one of the bottom face of first metal layer 902 and the top face of second metal layer 903.

A light supplied from light source 909, which is a type of electromagnetic source, to first metal layer 902 can be optically resonated between first boundary face 902B of first metal layer 902 and hollow area 904 and second boundary face 903A of second metal layer 903 and hollow area 904. If analyte 908C that establishes specific binding with acceptor 907 is present in sample 908, specific binding of acceptor 907 and analyte 908C is established, and thus a dielectric constant on first boundary face 902B and/or a dielectric constant on second boundary face 903A change. As a result, the optical resonance condition changes, and resonance absorption wavelength against light 909A supplied from light source 909 also changes. Detector 910 can detect this change as color change 909B. Visual detection can be used as one of detecting methods.

Optical sensor 900 does not need a prism. In addition, light 909A supplied from light source 909 does not need to have a certain polarization state or coherence. As a result, small and simple optical sensor 900 can be configured.

CITATION LIST

Patent Literature

PLT1: International Publication No. 2010/122776

SUMMARY OF THE INVENTION

The present invention offers an optical sensor with simple structure and high detection sensitivity. A first optical sensor of the present invention includes an input part, fixing part, and determining part. The input part is provided on the upper side of the sensor and configured to accept a sample into the sensor. The fixing part is provided below the input part and configured to dispose a carrier thereon. The carrier has an acceptor that reacts with an analyte in the sample and is fixed on a surface of the carrier. The determining part is provided to determine the presence of the analyte in the sample. The determining part includes a first metal layer, second metal layer, and hollow area. The first metal layer is configured to receive electromagnetic waves. The second metal layer faces the first metal layer. The hollow area is sandwiched between the first metal layer and the second metal layer. The input part, fixing part, and hollow area form a part of a passage where the sample flows from the input part toward the hollow area. In this structure, the analyte and the acceptor can sufficiently react when the analyte is present in the sample. This significantly changes the dielectric constant in the determining part, compared to other area. Therefore, this optical sensor achieves high detection sensitivity with a simple structure.

A second optical sensor of the present invention includes an input part and a determining part. The input part is configured to accept a sample into the sensor, and the determining part is configured to determine the presence of an analyte in the sample. The determining part is formed in the same way as that in the first optical sensor. A hollow area between the input part and the determining part form a part of a passage where the specimen flows from the input part to the hollow area. A protrusion that protrudes to the passage is formed upstream of the determining part in this passage. In this structure, if the analyte is present in the sample, an aggregate produced by reaction of this analyte and the acceptor does not reach the determining part, and a carrier containing the acceptor accumulates in the upstream of the protrusion. The dielectric constant in the determining part thus does not change. If the analyte is not present in the sample, an aggregate is not produced, and the carrier containing the acceptor accumulates in the determining part. The dielectric constant in the determining part thus significantly changes, compared to other areas. Accordingly, this optical sensor achieves high detection sensitivity with a simple structure.

DESCRIPTION OF EMBODIMENTS

Prior to describing exemplary embodiments of the present invention, disadvantages in optical sensor 900 in FIG. 9 are described. As described above, acceptors 907 are physically adsorbed on at least one of the bottom face of first metal layer 902 and the top face of second metal layer 903 in hollow area 904 of optical sensor 900. However, when the height (vertical length) of hollow area 904 is nano-sized, it is difficult to fix acceptors 907 on the metal layer in a sufficiently dispersed state. Therefore, acceptors 907 may gather at one part and are physically adsorbed in the aggregated state. In this case, a noise of optical sensor 900 increases.

In addition, a reaction area is hollow area 904 that is a nano-sized space. Therefore, acceptors 907 and analytes 908C may not sufficiently react even if acceptors 907 are sufficiently dispersed and fixed on the metal layer. As a result, detection sensitivity may not be sufficient.

The exemplary embodiments are described below with reference to drawings.

First Exemplary Embodiment

Figure 1:
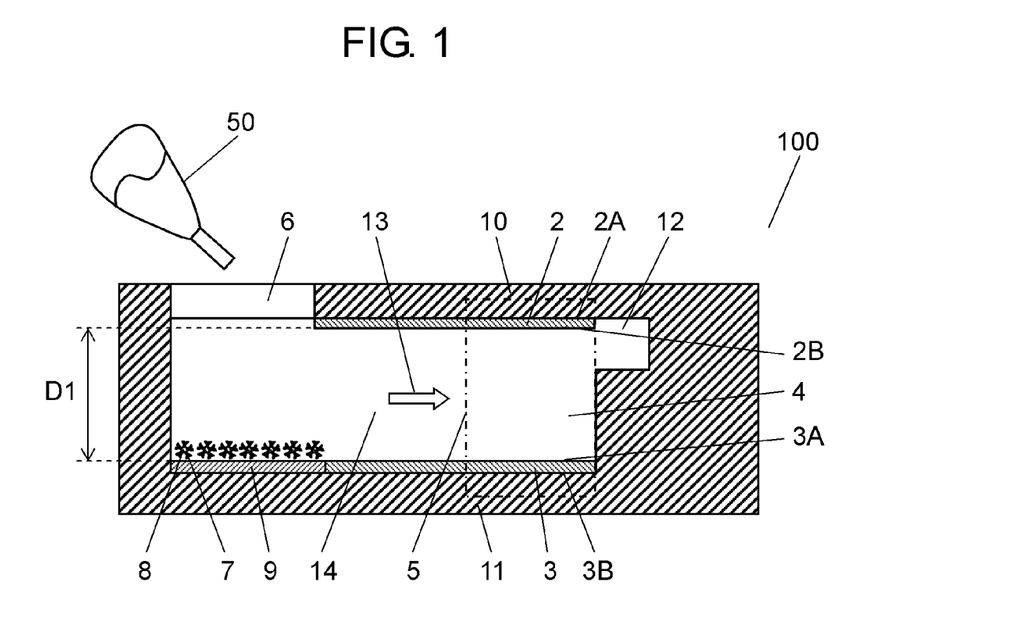
FIG. 1 is a sectional view of an optical sensor in accordance with a first exemplary embodiment of the present invention.
Figure 2:
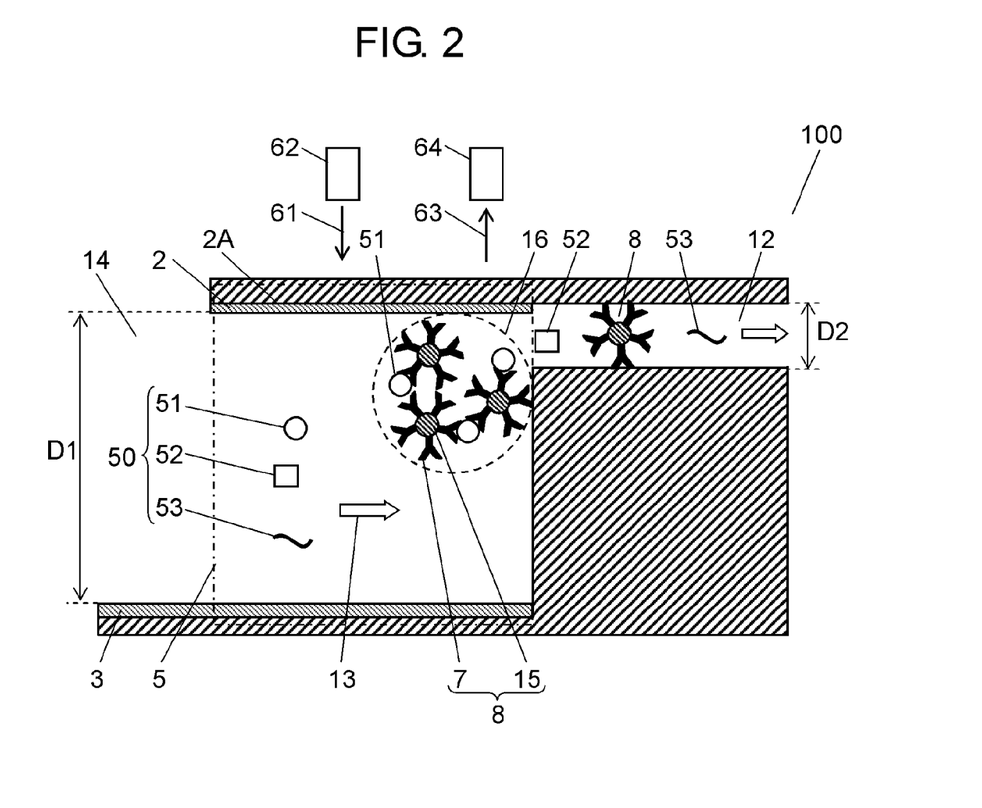
FIG. 2 is a sectional view of an essential part of the optical sensor shown in FIG. 1.

FIG. 1 is a schematic sectional view of optical sensor 100 in the first exemplary embodiment of the present invention. FIG. 2 is a sectional view of an essential part of optical sensor 100.

Optical sensor 100 is a MIM (Metal Insulator Metal) type sensor device.

Optical sensor 100 includes input part 6, fixing part 9, and determining part 5. Input part 6 is provided on the upper side and configured to accept sample 50. Fixing part 9 is provided below input part 6 and configured to dispose carrier 8. Acceptor 7 that reacts with analyte 51 in sample 50 is fixed on the surface of carrier 8. Determining part 5 is provided to determine the presence of analyte 51 in sample 50.

Determining part 5 includes first metal layer 2, second metal layer 3 (hereinafter referred to as metal layers 2 and 3), and hollow area 4. Metal layers 2 and 3 are formed of metal such as gold and silver. Metal layer 2 is configured to receive electromagnetic wave, and can transmit this electromagnetic wave. Metal layer 3 faces metal layer 2. Hollow area 4 is sandwiched between metal layer 2 and metal layer 3. Determining part 5 is configured such that the electromagnetic wave transmitted through metal layer 2 optically resonates between metal layer 2 and metal layer 3. In other words, metal layer 2 has top face 2A and bottom face 2B, and is configured to receive electromagnetic waves from above top face 2A. Metal layer 3 has top face 3A and bottom face 3B, and is configured to receive electromagnetic waves on top face 3A via metal layer 2 and hollow area 4. Top face 3A of metal layer 3 faces bottom face 2B of metal layer 2.

When the electromagnetic wave entering from top face 2A of metal layer 2 is a visible light and metal layer 2 is formed of gold, the thickness of metal layer 2 is preferably in a range from 5 nm to 45 nm. In other words, metal layer 2 can transmit lights including a visible light range as electromagnetic waves.

When metal layer 3 is formed of gold, the thickness of metal layer 3 is preferably 100 nm or more. When the thickness is less than 100 nm, entering electromagnetic wave may penetrate through metal layer 3, and thus an amount of electromagnetic wave reflected back to hollow area 4 is decreased.

Metal layers 2 and 3 are not limited to planar layers. They may be in a state that fine metal particles are spread on the surface.

Since the thickness of metal layer 2 is roughly 100 nm or below, metal layer 2 cannot retain its shape by itself. Top face 2A of metal layer 2 is fixed onto supporting part 10 to retain the shape. In the same way, metal layer 3 is fixed onto and retained by supporting part 11. Supporting part 10 needs to efficiently supply electromagnetic waves to metal layer 2. Therefore, supporting part 10 is formed of a material that causes less attenuation of electromagnetic waves. If the electromagnetic wave is a visible light, supporting part 10 is formed of a transparent material that efficiently transmits light, such as a glass and transparent plastic. The thickness of supporting part 10 is preferably as thin as possible within an allowable mechanical strength.

To increase sensitivity of optical sensor 100, it is preferable that supplied electromagnetic waves such as light do not penetrate metal layer 3. Accordingly, supporting part 11 is preferably formed of a material that blocks electromagnetic waves such as light. For example, supporting part 11 has preferably the thickness of 100 nm or more, and is formed of material such as metal and semiconductor in addition to glass and plastic.

Acceptor 7 is a capturing substance that establishes specific binding with analyte 51 that is a predetermined target substance. For example, acceptor 7 is antibody, receptor protein, aptamer, porphyrin, or polymer produced by molecular imprinting technology. Acceptors 7 are formed on the surface of core material 15 typically made of metal or resin to form carrier 8. Method of fixing acceptors 7 on core material 15 is not limited. For example, chemical adsorption is applicable. Acceptors 7 may be fixed onto core material 15 by silane coupling treatment or via self-assembled monomolecular membrane.

The size (diameter) of core material 15 is preferably 1/10 or less of the wavelength of the electromagnetic wave entering from above optical sensor 100. The wavelength here refers to a wavelength taking into account the influence of refractive index in hollow area 4. If the size of core material 15 is greater than 1/10 of wavelength of the entering electromagnetic wave, influence of Mie scattering becomes large. On the other hand, if the size of core material 15 is not greater than 1/10 of wavelength of the entering electromagnetic wave, influence of Rayleigh scattering becomes large. The scattering strength of Rayleigh scattering is proportional to $radius^{-6}$, which is extremely small. The influence of scattering can thus be mostly ignored. Accordingly, sensitivity of optical sensor 100 can be improved. For example, if a visible light (in particular, light with wavelength from 500 to 600 nm used for observation) is used as the electromagnetic wave entering from above optical sensor 100, the size of core material 15 is preferably 50 to 60 nm or less. When the influence of scattering is large, straightness of light is lost, and a light to be observed may not be sufficiently observed.

Carrier 8 is disposed on fixing part 9. Therefore, fixing part 9 is preferably made of a material that enables to easily fix carrier 8. For example, fixing part 9 is made of polymer, metal, ceramics, glass, or silicon. In view of ease of process, fixing part 9 is made of metal, and is preferably formed integrally with metal layer 3 formed in hollow area 4. In particular, glass or metal is preferable, for example, as a material that enables easy fixing of carrier 8. If glass or metal is used, surface treatment for fixing is easy Carrier 8 is preferably disposed on fixing part 9 by physical adsorption. In other words, it is preferable that fixing part 9 can physically adsorb carrier 8. Physical adsorption employs the Van der Waals force that acts on a boundary face of fixing part 9 and carrier 8 and a boundary face of carriers 8. Carrier 8 is fixed by mixing it typically with a solution, dripping the solution containing carrier 8 onto fixing part 9, and drying it.

Meanwhile, as another method of disposing carrier 8 on fixing part 9, chemical binding may be employed. When chemical binding is used for placement, carrier 8 is preferably disposed in the binding state such that it is easy to be released from fixing part 9 when sample 50 is input.

Still more, fixing part 9 is preferably configured with a material that carrier 8 is easily releasable. For example, one method is applying a release-accelerating layer (not illustrated) to the surface of fixing part 9. The release-accelerating layer is formed of a constituent soluble or decomposable by a constituent in the sample. If sample 50 is saliva, the release-accelerating layer can be formed typically by applying starch to the surface of fixing part 9. Starch dissolves by enzyme (e.g., amylase) contained in saliva, Carrier 8 is fixed after forming the release-accelerating layer. By forming the release-accelerating layer, carrier 8 can be efficiently released from fixing part 9 when sample 50 is input into optical sensor 100

Another method of facilitating the release of carrier 8 from fixing part 9 is a method of covering carrier 8 with the release-accelerating layer. In this case, carrier 8 is covered with the release-accelerating layer, and then carrier 8 covered with the release-accelerating layer is fixed on fixing part 9, thereby fixing carrier 8 on fixing part 9. Also in this case, formation of the release-accelerating layer enables to efficiently release carrier 8 from fixing part 9 when sample 50 is input into optical sensor 100.

Carriers 8 disposed on fixing part 9 is physically fixed by a weak force such as the Van der Waals force. Therefore, when sample 50 is input from input part 6, carriers 8 are released from fixing part 9 by the flow of sample 50, carried along in a direction of arrow 13, and suspended in hollow area 4. As described above, input part 6, fixing part 9, and hollow area 4 form a part of a passage in which sample 50 flows from input part 6 toward hollow area 4.

A portion between fixing part 9 and determining part 5 can be used as reaction area 14 where carriers 8 and sample 50 react with each other. If carriers 8 react with sample 50 quickly, the portion between fixing part 9 and determining part 5 may be short or unnecessary. In other words, fixing part 9 and determining part 5 may be next to each other.

Figure 3:
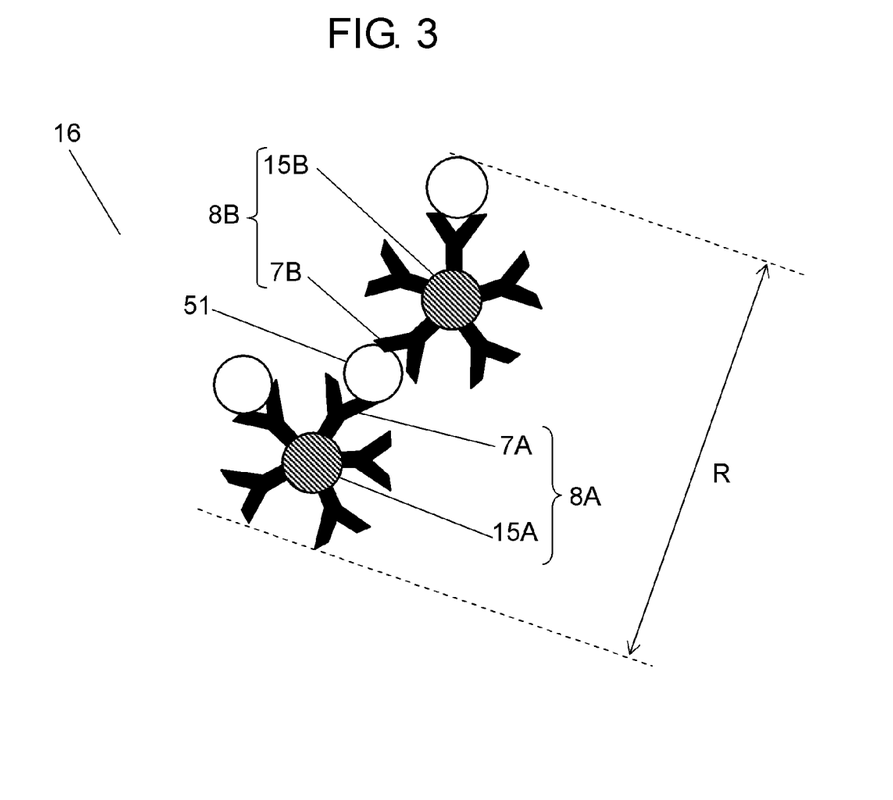
FIG. 3 is a conceptual diagram when an aggregate is formed in the optical sensor shown in FIG. 1.

Sample 50 contains medium 53 that is fluid, such as liquid and gel; analyte 51 that is a specimen, and non-specific specimen 52. When analyte 51 that specifically reacts with acceptor 7 exists in sample 50, analyte 51 and acceptor 7 cause specific reaction and form aggregate 16. How aggregate 16 is formed is described with reference to FIG. 3. FIG. 3 is a conceptual diagram illustrating specific binding of acceptor 7 and analyte 51 when sample 50 contains analyte 51.

Acceptor 7 on the surface of carrier 8 does not specifically bind with non-specific specimen 52, but selectively causes specific binding only with analyte 51. Then, multiple carriers 8 bind via analyte 51 to form aggregate 16.

In the example shown in FIG. 3, carrier 8A includes core material 15A and multiple acceptors 7A fixed on the surface of core material 15A. One of acceptors 7A specifically binds with analyte 51. Carrier 8B includes core material 15B and multiple acceptors 7B fixed on the surface of core material 15B. One of acceptors 7B specifically binds with analyte 51. In this way, carriers 8A and 8B bind with analyte 51 therebetween to form aggregate 16. Carriers 8A and 8B have multiple acceptors 7A and 7B, respectively.

Therefore, multiple acceptors 7A and 7B specifically bind with still other analytes 51 so that further more carriers are bound. This enables to form larger aggregate 16.

As described above, aggregate 16 is formed by binding of multiple carriers 8 via analyte 51, and thus a range of shapes may be formed. In the description, aggregate 16 refers to that formed by binding at least two or more carriers 8. Its diameter refers to maximum diameter R of aggregate 16 shown in FIG. 3.

Determining part 5 traps aggregate 16 to determine the presence of analyte 51 in sample 50.

Already-inspected sample 50 flowing in hollow area 4 of determining part 5 goes to discharge area 12 and is retained there. Discharge area 12 is connected to hollow area 4, and is located downstream of hollow area 4 in the passage of sample 50. Height (vertical length) D1 of hollow area 4 and height (vertical length) D2 of discharge area 12 are designed to satisfy the relation D1>D2. In other words, height D2 of discharge area 12 is shorter than height D1 of hollow area 4 (a distance between bottom face 2B of metal layer 2 and top face 3A of metal layer 3A). Height D2 of discharge area 12 is designed to pass medium 53, non-specific specimen 52, and carrier 8 causing no reaction with analyte 51, and not to pass aggregate 16. In other words, height D2 is set to a value larger than the diameter of carrier 8 and smaller than diameter R of aggregate shown in FIG. 3. As a result, aggregate 16 is trapped in determining part 5. For example, height D1 is set to 700 to 1000 nm, and height D2 is set to 350 to 750 nm. In this case, sample 50 moves in the passage by capillary action rather than flowing in a general sense.

In order to encourage a smooth flow of sample 50 in the passage, the width (a length in a direction perpendicular to arrow 13 and height D1) of hollow area 4 is designed to about 5 to 10 mm. Accordingly, it becomes difficult to pass sample 50 if the width of discharge area 12 is narrowed to trap aggregate 16 in hollow area 4. Accordingly, aforementioned D1>D2 is preferable.

Next, the operation of optical sensor 100 is described with reference to FIG. 2 and FIGS. 4 to 6. As shown in FIG. 2, electromagnetic source 62 is disposed over top face 2A of metal layer 2. Electromagnetic source 62 applies electromagnetic wave 61 to metal layer 2 from above top face 2A of metal layer 2. In the exemplary embodiment, electromagnetic wave 61 is a light, and electromagnetic source 62 is a light source. Preferable electromagnetic source 62 is a source of a visible light that human can easily detect a change of wavelength without using a special detector.

A part of electromagnetic wave applied from above metal layer 2 to top face 2A at incident angle θ (not illustrated) is reflected on top face 2A and bottom face 2B, and propagates upward from metal layer 2 in the direction of reflection angle −θ (not illustrated). Angle θ is an angle formed by the vertical direction of metal layer 2 and entering direction of electromagnetic wave. In electromagnetic waves entering from above metal layer 2, electromagnetic wave propagating upward from metal layer 2 in the direction of angle −θ is referred as a first electromagnetic wave.

However, a large portion of electromagnetic waves not reflected on top face 2A and bottom face 2B of metal layer 2 penetrate metal layer 2, propagates in hollow area 4, and reaches top face 3A of metal layer 3. When metal layer 3 is sufficiently thick, which is 100 nm or more, the electromagnetic waves coming from above metal layer 3 are completely reflected on metal layer 3, and propagate again in hollow area 4 toward bottom face 2B of metal layer 2. A part of the electromagnetic waves reaching bottom face 2B of metal layer 2 penetrate metal layer 2, and propagates upward from metal layer 2 in the direction of angle −θ. In the description below, this electromagnetic wave penetrating metal layer 2 from hollow area 4 and propagating upward from metal layer 2 in the direction of angle −θ is referred as a second electromagnetic wave.

A large portion of the electromagnetic waves reaching bottom face 2B of metal layer 2 but not penetrating metal layer 2 is reflected on bottom face 2B or top face 2A of metal layer 2, and propagates again downward in hollow area 4. Here, the first electromagnetic wave and the second electromagnetic wave interfere each other above metal layer 2. In particular, the first and second electromagnetic waves weaken each other when a condition of Formula 1 is satisfied. Contrarily, they enhance each other when a condition of Formula 2 is satisfied.

$$(m+\tfrac{1}{2})\times\lambda = 2\times n\times d\times\cos\theta \quad \text{(Formula 1)}$$

m: Integer
λ: Wavelength of electromagnetic wave (wavelength in vacuum)
d: Height of hollow area (D1)
θ: Angle formed by the vertical direction of metal layer 2 and entering direction of electromagnetic wave $$m\times\lambda = 2\times n\times d\times\cos\theta \quad \text{(Formula 2)}$$

These interference conditions are controllable mainly by thickness among shapes of metal layer 2 and metal layer 3, distance between metal layer 2 and metal layer 3, dielectric constant (refractive index) of metal layer 2, dielectric constant (refractive index) of metal layer 3, and refractive index in hollow area 4.

As shown in FIG. 2, detector 64 capable of detecting electromagnetic wave 63 such as light is disposed over top face 2A of metal layer 2. When optical sensor 100 receives electromagnetic wave 61 given from electromagnetic source 62, detector 64 receives reflected or radiated electromagnetic wave 63, such as light, from optical sensor 100. However, detector 64 is not always necessary. If electromagnetic wave 61 is a visible light, the user himself/herself can detect a change of color and a strength of electromagnetic wave 61 by his/her eyes. Accordingly, optical sensor 100 can be used simply and inexpensively.

As shown in FIG. 2, when determining part 5 traps aggregate 16, aggregate 16 coming next is blocked in hollow area 4 by aggregate 16 that is already trapped. By repetition of this process, aggregates 16 stay in hollow area 4 of determining part 5. In other words, carrier 8, non-specific specimen 52, and medium 53 that have diameters smaller than that of aggregate 16 in sample 50 can pass determining part 5, but aggregate 16 that has a diameter larger than that of carrier 8 cannot pass determining part 5.

Retention of aggregate 16 in determining part 5 changes dielectric constant (refractive index) of medium 53 between metal layers 2 and 3, and distribution of the dielectric constant. As a result, electromagnetic wavelength λ changes due to mutually enhancing or weakening electromagnetic waves over metal layer 2. Electromagnetic wavelength λ is obtained according to Formula 1 and Formula 2. In other words, frequency distribution of electromagnetic waves detected by detector 64 (i.e., interference between electromagnetic waves) changes.

As a result, when light including a visible light range enters optical sensor 100 as incident wave, the color of light propagating upward from metal layer 2 changes, compared to that before inputting sample 50. The presence of analyte 51 in sample 50 can be confirmed by detecting this change of light color by human eyes.

On the other hand, if analyte 51 is not present in sample 50, no aggregate 16 is formed, and thus carrier 8 on which acceptors 7 are fixed is carried along with sample 50. Therefore, unlike the case when analyte 51 is present and aggregate 16 is formed, there is no change in dielectric constant in determining part 5. Interference between electromagnetic waves propagating upward from metal layer 2 also does not change. As a result, the color of light propagating upward from metal layer 2 does not change, compared to that before inputting the sample, even if the light including a visible light range enters optical sensor 100 as incident wave. By detecting a change of the state of electromagnetic wave propagating upward from metal layer 2, the presence of specific binding in hollow area 4 of determining part 5 can be confirmed. In other words, also at home, the user can easily confirm the presence of analyte (e.g., virus) by using optical sensor 100.

In order to use optical sensor 100 as a home sensor, optical sensor 100 requires to have higher detection sensitivity and be easier to use than that of industrial sensors used typically at hospitals.

In optical sensor 100, hollow area 4 and an area where hollow area 4 is not formed are integrated. Fixing part 9 for disposing carrier 8 is provided in the area where hollow area 4 is not formed. Therefore, carrier 8 can be easily fixed onto fixing part 9.

In addition, since input part 6 is formed at an upper part of optical sensor 100, sample 50 can be easily input. Furthermore, fixing part 9 for fixing carrier 8 is provided below input part 6. In other words, input part 6 is formed over fixing part 9, and thus carrier 8 can be easily fixed onto fixing part 9 from input part 6.

For fixing carrier 8, surface treatment is preferably applied to fixing part 9. Since fixing part 9 is provided at a position different from hollow area 4 in optical sensor 100, surface treatment can be easily applied to fixing part 9 independently of height D1 of hollow area 4. As a result, carrier 8 can be fixed in the state sufficiently dispersed in optical sensor 100. And, carrier 8 can be easily released when sample 50 is input.

In accordance with the flow of sample 50, carrier 8 is carried to hollow area 4 along with sample 50, and aggregate 16 is formed due to specific reaction only when analyte 51 is present. In other words, as described above, a portion from fixing part 9 to determining part 5 in optical sensor 100 can be used as reaction area 14 where carrier 8 and sample 50 react with each other. Accordingly, sufficient reaction time can be secured, compared to the case of fixing acceptors 7 in hollow area 4. In addition, since a frequency of contact with acceptors 7 and carriers 8 can be increased, reaction will reliably take place. As a result, optical sensor 100 achieves high detection sensitivity.

In optical sensor 100, carriers 8 each on which acceptors 7 are fixed are disposed inside optical sensor 100. Therefore, the user can easily conduct inspection just by dripping sample 50, which is a specimen.

Based on the above reasons, input part 6 is preferably provided right above fixing part 9. This layout facilitates fixing of carrier 8 onto fixing part 9, and also facilitates release of carrier 8 from fixing part 9 when sample 50 is input to optical sensor 100.

Preferably, a filter (not illustrated) is disposed on input part 6. Unnecessary particles, such as dust, mixed in sample 50 can be removed by the filter.

Metal layer 2 and metal layer 3 may be formed at least on the upper side and lower side of determining part 5, respectively. Materials of the top face and the bottom face of discharge area 12 are not limited, but they are preferably made of the same material as hollow area 4, i.e., metal layers 2 and 3, with respect to processes.

Reaction area 14 is an area between fixing part 9 and determining part 5. However, a portion above fixing part 9, i.e., a portion from input part 6 to fixing part 9, can also be used as reaction area 14. In FIG. 1, the top face and the bottom face of reaction area 14 are configured with metal layers 2 and 3, and the height of reaction area 14 is same as height D1 of hollow area 4. However, the height of reaction area 14 is preferably greater than D1. For example, if input part 6 is formed right above fixing part 9 and reaction area 14, this condition can be achieved.

Still more, a structure for retaining the aggregate inside determining part 5 may be provided in order to prevent an easy escape of aggregate 16 from determining part 5 by the flow (arrow 13) of sample 50. For example, portions of surfaces of metal layers 2 and 3 facing determining part 5 may be roughened to provide a structure to increase a friction factor.

Still more, determining part 5 includes hollow area 4, and further preferably includes a connecting part of hollow area 4 and discharge area 12. This can easily reflect the influence of aggregate 16.

Still more, a suction material may be provided in discharge area 12 to suction sample 50 in hollow area 4. Or, a pressure inside discharge area 12 may be kept lower than atmospheric pressure to vacuum sample 50 by a pressure difference caused by opening discharge area 12 to hollow area 4 at the same time as inputting sample 50.

A storage part (not illustrated) may be provided beyond discharge area 12. Or, discharge area 12 may be communicated with outside optical sensor 100. However, it is preferable to have a structure not to discharge evaluated sample 50 outside. If the storage part is provided, the height (vertical length) of the storage part is preferably longer than the height of discharge area 12. By enlarging the volume of the storage part, sample 50 can continues to permeate by capillary action. This can encourage reaction.

Additionally, an ultrasonic wave generating source (not illustrated) is preferably provided at a part of each of bottom face 2B of metal layer 2 and top face 3A of metal layer 3. The use of ultrasonic wave also enables to accelerate aggregation. Accordingly, carrier 8 that is present at an upper part of hollow area 4 moves by ultrasonic wave generated from the ultrasonic wave generating source, and likely binds with analyte 51. In addition, a standing wave of ultrasonic wave is generated between metal layers 2 and 3, and a phenomenon of collecting carriers 8 and analytes 51 to a predetermined area between metal layers 2 and 3 occurs. Accordingly, probability of binding of carrier 8 and analyte 51 is increased.

Still more, a heater (not illustrated) as a heat source is preferably provided on the top face of supporting part 10. This structure increases motion energy of carrier 8 and analyte 51 by heating sample 50 in hollow area 4 to accelerate specific binding. For example, accelerated motions of carrier 8 and analyte 51 increase their probability of contact. This likely generates aggregate 16 by specific binding. By heating hollow area 4 of optical sensor 100 in this way, there will be more chance of specific binding of carrier 8 and analyte 51. Aggregation of analyte 51 can thus be accelerated. The place of installing the heater is not limited.

Still more, a magnetic field generating source (not illustrated) is provided near each of the top face of supporting part 10 and the bottom face of supporting part 11, and core material 15 of carrier 8 is preferably formed of a magnetic body so as to be attracted in a magnetic field direction. When a magnetic field is generated from top to bottom of hollow area 4 in this structure, carrier 8 is attracted to the magnetic field and likely binds with analyte 51. By generating the magnetic field in the vertical direction of hollow area 4 of optical sensor 100 in this way, there will be more chance of specific binding of carrier 8 and analyte 51. Aggregation of analyte 51 can thus be accelerated. Instead of providing the magnetic field generating source, a magnetic field generator held by user's hand may be used for applying the magnetic field to hollow area 4.

Figure 4:
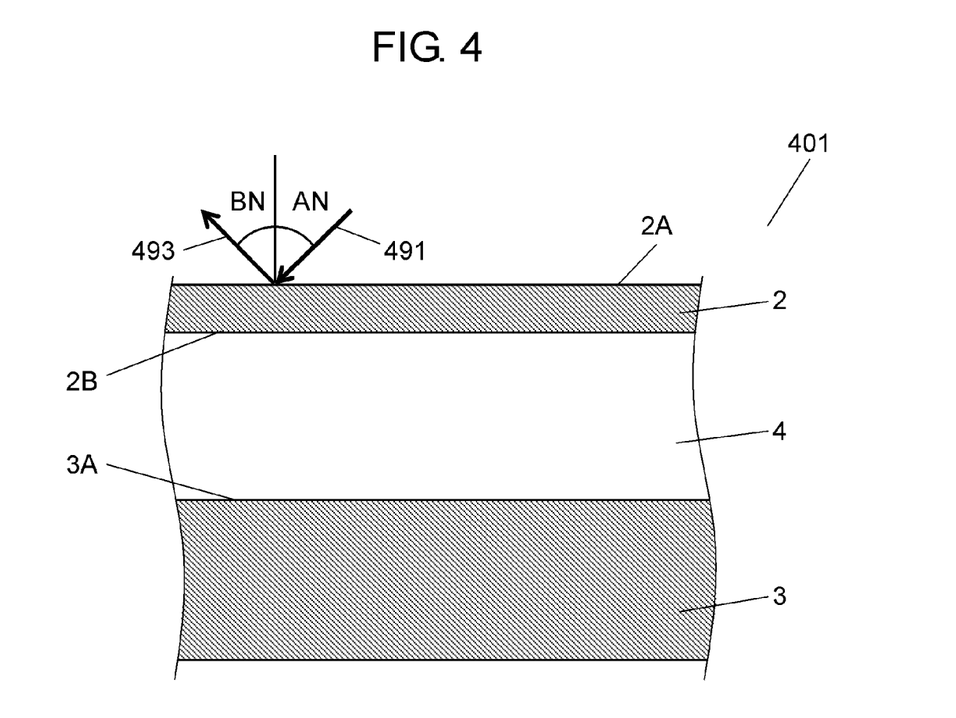
FIG. 4 is a conceptual diagram of an analysis model of electromagnetic field simulation of the optical sensor shown in FIG. 1.

Next is described how the state of electromagnetic waves propagating upward from metal layer 2 of the optical sensor changes by specific binding of acceptor 7 and analyte 51, using results of an electromagnetic field simulation, with reference to FIG. 4. FIG. 4 is a conceptual diagram of an analysis model of the electromagnetic field simulation of optical sensor 100.

Determining part 5 of optical sensor 100 shown in FIG. 1 is used in analysis model 401 shown in FIG. 4. Metal layer 2 is formed of silver, and is 30 nm thick. Metal layer 3 is formed of silver, and is 130 nm thick. A distance between metal layers 2 and 3 is 160 nm. Hollow area 4 is filled with air whose relative dielectric constant is 1. The area over top face 2 of metal layer 2 and the area below bottom face 3B of metal layer 3 are filled with air. In analysis model 401, electromagnetic wave 491 enters metal layer 2 at incident angle AN, and electromagnetic wave 493 propagates upward from metal layer 2 at angle BN (−AN). They are simulated and analyzed. In analysis model 401, metal layers 2 and 3 and hollow area 4 endlessly continue in the horizontal direction.

In optical sensor 100, in addition to a change of frequency or wavelength that mutually weakens the first electromagnetic wave and the second electromagnetic wave, a change of reflectance is detected. These two indices can be simultaneously used to detect changes of the state of the medium in hollow area 4. Accordingly, optical sensor 100 can demonstrate high detection capability. Note that reflectance refers to a value obtained by using an amount of energy of electromagnetic wave entering from above metal layer 2 of optical sensor 100 as a denominator, and an amount of energy of electromagnetic wave propagating upward from metal layer 2 as a numerator.

Figure 5:
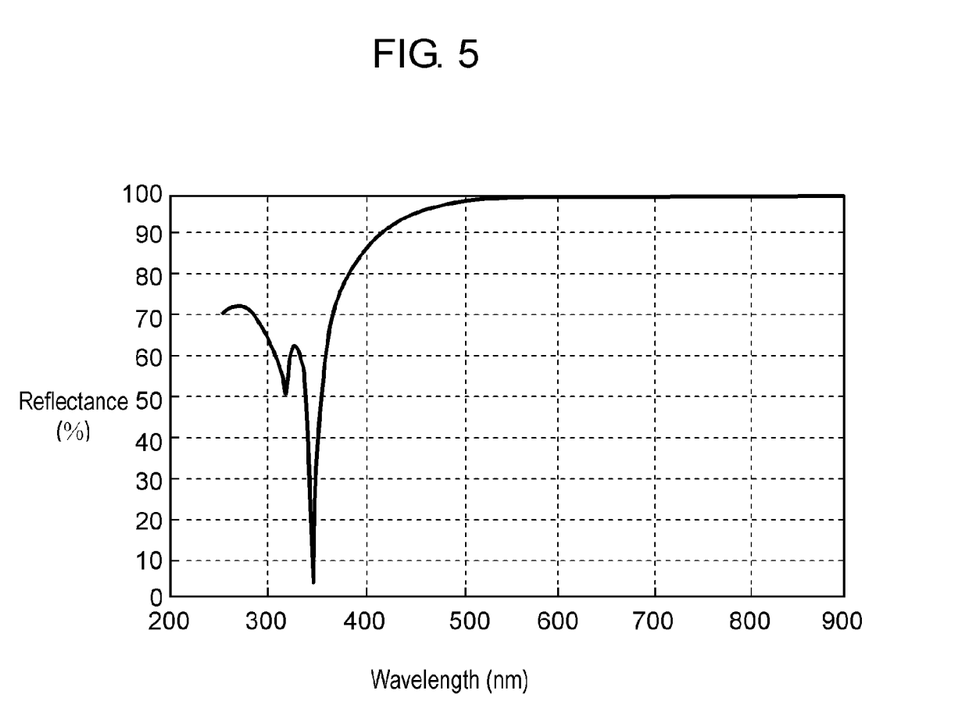
FIG. 5 is an analysis result of electromagnetic field simulation of optical sensor shown in FIG. 1.

The state of the medium in hollow area 4 is a state of substance filled in a part or all of hollow area 4. For example, the state indicates composition of the substance itself or distribution of substance in hollow area 4. FIG. 5 is a graph showing analysis results of the model in FIG. 4. The horizontal axis is wavelength, and the vertical axis is reflectance. It is also apparent from FIG. 5 that reflectance drastically reduces when the condition of Formula 1 is satisfied at wavelengths around 340 nm and electromagnetic waves cancel each other.

Figure 6:
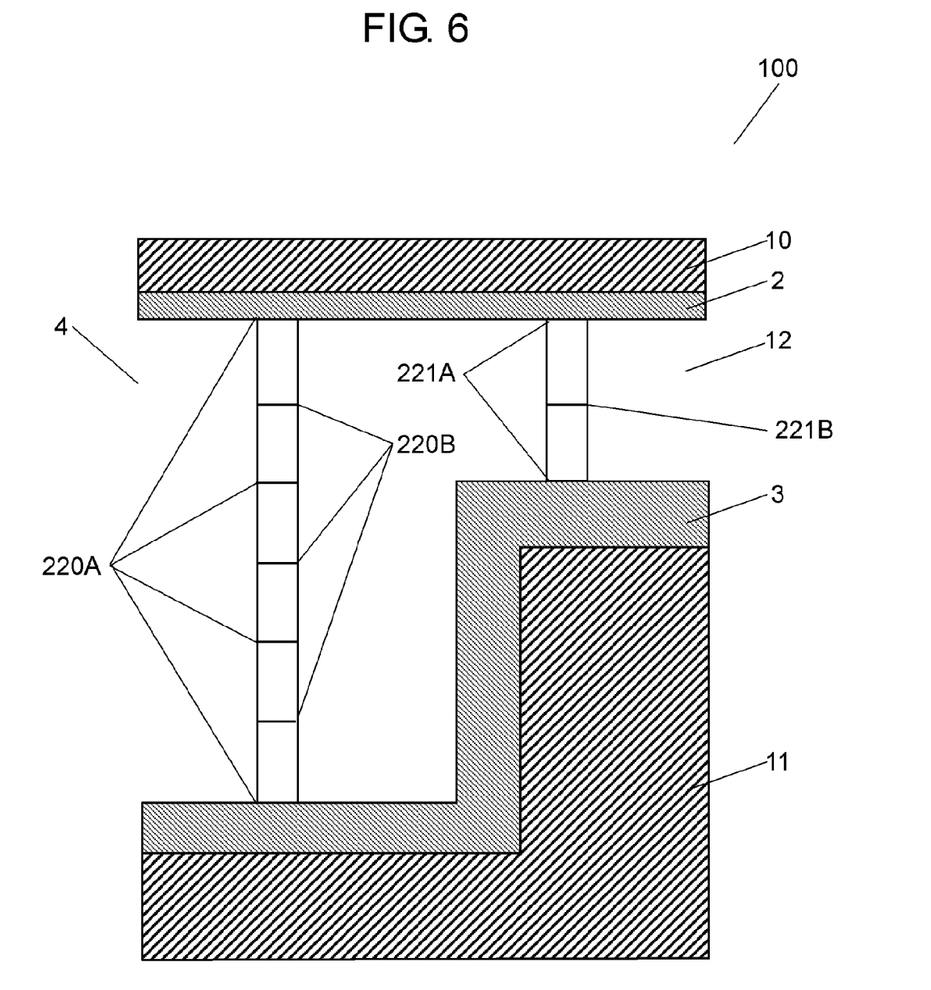
FIG. 6 is a chart illustrating distribution of electromagnetic strength in a passage of the optical sensor shown in FIG. 1.

FIG. 6 shows distribution of electric intensity in the passage of optical sensor 100. When the upper face of discharge area 12 is formed of metal layer 2 and the bottom face is formed of metal layer 3 in optical sensor 100, the interference state of electromagnetic waves propagating upward from hollow area 4 of metal layer 2 and the interference state of electromagnetic waves propagating upward from discharge area 12 of metal layer 2 may be roughly adjusted to the same state. More specifically, the height of hollow area 4 and the height of discharge area 12 are both designed based on Formula 1. Or, both are designed based on Formula 2. However, possible value "m" in Formula 1 or Formula 2 for hollow area 4 is different from that for discharge area 12.

At part 220A, the first electromagnetic wave and the second electromagnetic wave satisfy the condition of Formula 2 and weaken each other in hollow area 4. At part 220B, the first electromagnetic wave and the second electromagnetic wave satisfy the condition of Formula 1 and enhance each other in hollow area 4. At part 221A, the first electromagnetic wave and the second first electromagnetic wave satisfy the condition of Formula 2 and weaken each other in discharge area 12. At part 221B, the first electromagnetic wave and the second electromagnetic wave satisfy the condition of Formula 1 and enhance each other in discharge area 12.

In this way, when the light in a visible light range, for example, is supplied from above metal layer 2 of optical sensor 100, colors of reflective lights from an area of metal layer 2 in contact with hollow area 4 and an area of metal layer 2 in contact with discharge area 12 become roughly the same. Therefore, when analyte 51 and acceptor 7 of carrier 8 are specifically bound and aggregate 16 is formed and trapped in hollow area 4, many aggregates 16 stay in determining part 5. Then, the color of reflective light from the area of metal layer 2 in contact with hollow area 4 obviously changes. Accordingly, the user at home can easily confirm the presence of analyte, using optical sensor 100.

In order that the user detects the presence of analyte 51 by detecting the color change in optical sensor 100, a light source in a visible light range is preferably used as the light source. Note that the visible light range is an optical wavelength range that is noticeable by human eyes, and is within a wavelength range from 380 nm to 750 nm, inclusive. For example, optical sensor 100 is designed to satisfy the condition of Formula 2 at wavelengths from 580 to 600 nm, which is orange to red visible light range, in the state a sample without analyte is input to optical sensor 100. Then, compositions of carrier 8 may be selected or a structure of hollow area 4 may be determined to satisfy Formula 2 at wavelength of reflective light of 560 nm or shorter from the area of metal layer 2 in contact with hollow area 4 when sample 50 containing analyte 51 is input from input part 6. This causes a change of wavelength of reflective light across wavelengths of yellow (around a range from 560 to 580 nm) that shows a large color difference noticeable by human eyes. Therefore, the user at home or the like can easily confirm the occurrence of specific binding.

Still more, a filter that only passes a predetermined wavelength may be disposed between above optical sensor 100 and observer's eyes. In the above example, a filter that does not pass wavelengths shorter than 580 nm is disposed. In this case, when the sample does not contain analyte 51, the light looks bright because a light of 580 nm or higher is transmitted. When sample 50 contains analyte 51, wavelengths satisfying the condition of Formula 2 are attenuated by the filter, and thus the light looks dark. In some cases, a brightness difference is more easily noticed than color difference. This structure may be more effective in these cases.

Figure 7A:
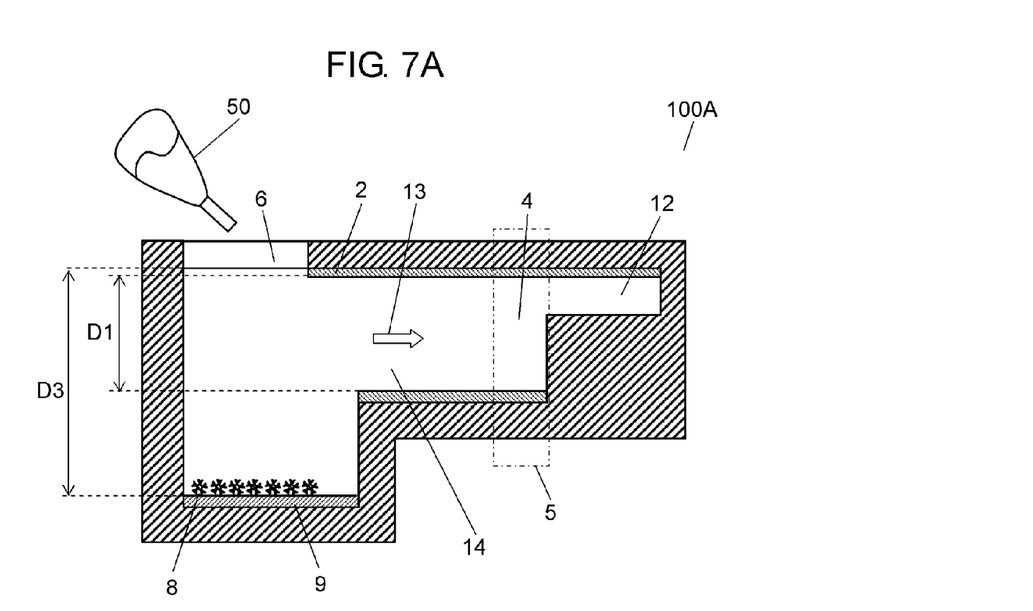
FIG. 7A is a sectional view of an essential part of another optical sensor in accordance with the first exemplary embodiment of the present invention.
Figure 7B:
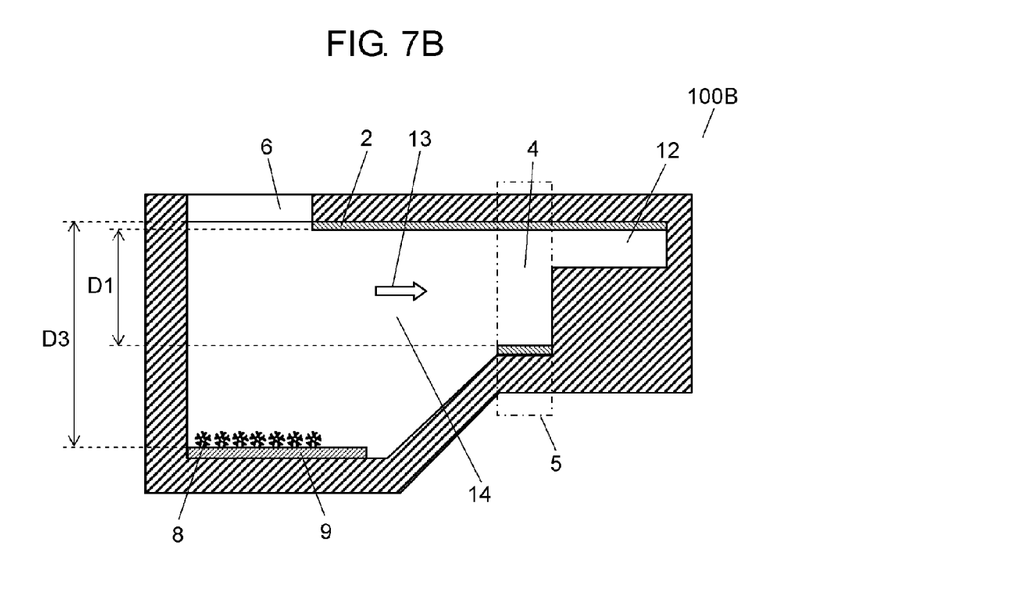
FIG. 7B is a sectional view of an essential part of still another optical sensor in accordance with the first exemplary embodiment of the present invention.

FIGS. 7A and 7B are sectional views of other optical sensors 100A and 100B in the exemplary embodiment. In optical sensors 100A and 100B, fixing part 9 is formed on a face lower than the bottom face of hollow area 4 where determining part 5 is formed. In other words, height D3, which is the height from top face 2A of metal layer 2 to fixing part 9, is longer than height D1 of hollow area 4.

With this structure, carriers 8 can be fixed only on fixing part 9 in such a manner that the solution containing carriers 8 does not flow to determining part 5 when carriers 8 are mixed with solution to fix carriers 8 onto fixing part 9. In case of optical sensors 100A and 100B, an area from input part 6 to fixing part 9 can also be sufficiently used as the reaction area.

Still more, as shown in FIG. 7B, the bottom face between fixing part 9 and determining part 5, which is the bottom face of reaction area 14, may be sloped. This shape enables to efficiently move sample 50, carriers 8, and reacted aggregates 16 to determining part 5. In addition, applying surface treatment to the bottom face of reaction area 14 allows sample 50 and so on to further easily move.

Second Exemplary Embodiment

Figure 8A:
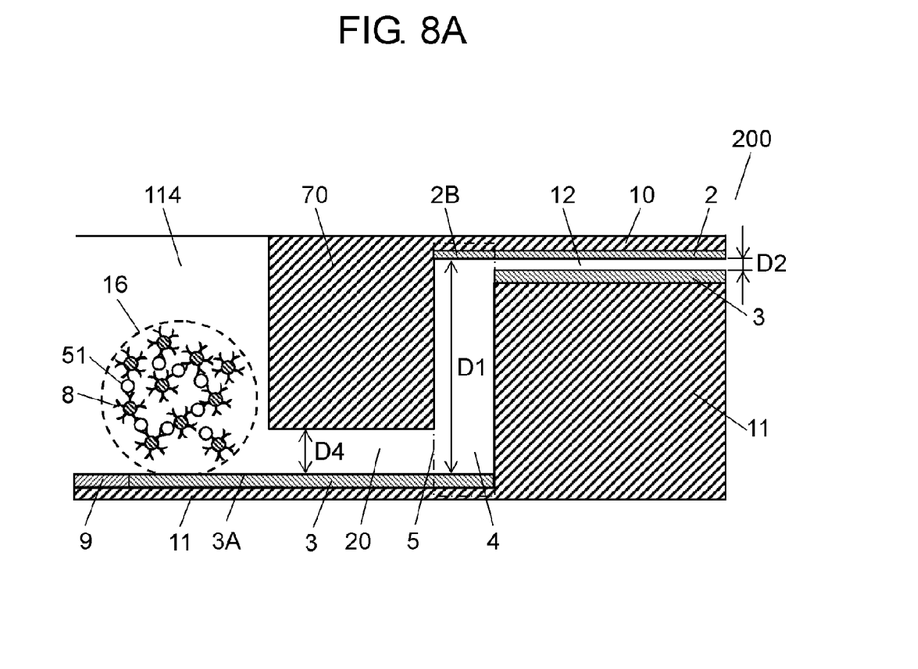
FIG. 8A is a sectional view of an essential part when analyte is present in a sample in an optical sensor in accordance with a second exemplary embodiment of the present invention.
Figure 8B:
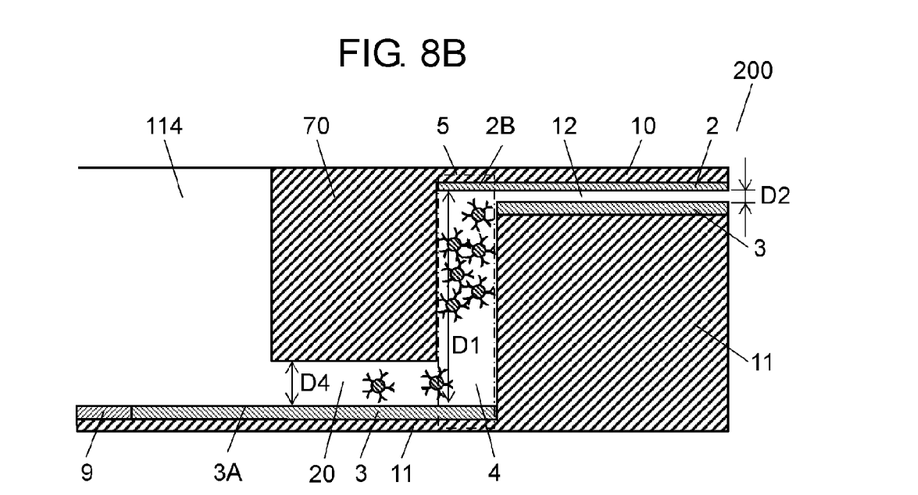
FIG. 8B is a sectional view of the essential part when analyte is not present in the sample in the optical sensor shown in FIG. 8A.

FIGS. 8A and 8B are sectional views of an essential part of optical sensor 200 in the second exemplary embodiment of the present invention. In this exemplary embodiment, components same as the first exemplary embodiment are given the same reference marks to omit their detailed description. Optical sensor 200 is different from optical sensor 100 in the first exemplary embodiment in that protrusion 70 is provided between fixing part 9 and determining part 5. Protrusion 70 is provided upstream of determining part 5 in the passage, and protrudes to the passage to partially reduce the height of the passage. In other words, narrowed area 20 with a height shorter than the height of hollow area 4 is provided between the bottom face of protrusion 70 and top face 3A of metal layer 3. Although not illustrated, structures of input part 6 and fixing part 9 are same as that of the first exemplary embodiment.

At the upstream side of determining part 5, reaction area 114, where carrier 8 with acceptors 7 released from fixing part 9 and sample 50 react, is provided. Protrusion 70 protruding downward from the top face of optical sensor 200 is formed between reaction area 114 and determining part 5. In other words, protrusion 70 is formed on the top face upstream of determining part 5.

Protrusion 70 is integrally formed with supporting part 10, for example. A material of a face opposing protrusion 70 is not specified, but a material equivalent to metal layer 3 or fixing part 9 is preferable in view of the ease of process. In FIGS. 8A and 8B, the face opposing protrusion 70 is formed of metal layer 3.

The height of narrowed area 20 in the passage below protrusion 70, i.e., distance (height of passage) D4 between the bottom face of protrusion 70 and top face 3A of metal layer 3, is designed to a dimension that passes carrier 8 but not aggregate 16. In other words, D4 is smaller than the size of aggregate 16 and larger than the size of the carrier. Protrusion 70 is designed to achieve this size for D4. The size of aggregate 16 refers to maximum diameter R of aggregate 16 shown in FIG. 3. Discharge area 12 is provided beyond determining part 5. Height D2 of discharge area 12 is shorter than the size of carrier 8.

FIG. 8A shows the case that analyte 51 is present in sample 50. In this case, analyte 51 and acceptors 7 fixed on the surface of carrier 8 specifically bind together, and form aggregate 16. Since aggregate 16 cannot pass below protrusion 70, it stays in reaction area 114. Accordingly, aggregate 16 does not reach determining part 5. Therefore, a dielectric constant of determining part 5 does not change, and the interference state between the electromagnetic waves propagating upward from metal layer 2 also does not change. As a result, even if a light containing a visible light range enters optical sensor 200 as the incident wave, the color of light propagating upward from metal layer 2 does not change, compared to that before inputting the sample.

FIG. 8B shows the case that analyte 51 is not present in sample 50. In this case, no aggregate 16 is formed, and thus carriers 8 onto which acceptors 7 are fixed stay in sample 50 as they are. Since the size of carrier 8 is smaller than passage height D4 below protrusion 70, carriers 8 reach determining part 5. However, since the size of carrier 8 is larger than height D2 of discharge area 12, carriers 8 gradually accumulate in determining part 5. Then, an agglomerate of carriers 8 is formed in determining part 5. As a result, a dielectric constant (refractive index) of medium 53 between metal layers 2 and 3 and distribution of dielectric constant change, and the electromagnetic wave mutually enhances or weakens above metal layer 2, and thus electromagnetic wavelength λ changes. In other words, the frequency distribution of the electromagnetic waves (i.e., interference state between the electromagnetic waves) detected by the detector changes. Electromagnetic wavelength λ is calculated according to Formula 1 and Formula 2.

As a result, when light including a visible light range enters optical sensor 200 as the incident wave, the color of light propagating upward from metal layer 2 changes, compared to that before inputting sample 50. By detecting this change of light color with human eyes, the presence of analyte 51 in sample 50 can be confirmed.

Passage height D4 below protrusion 70 may increase from the downstream to upstream sides. This structure makes carriers 8 not forming aggregate 16 easier to pass below protrusion 70.

As described above, detecting the state of change of electromagnetic waves propagating upward from metal layer 2 allows the presence of specific binding in hollow area 4 of determining part 5 to be confirmed. Optical sensor 200 eliminates erroneous determination that may occur due to a change of dielectric constant caused by non-specific adsorption occurred by entry of aggregate 16 into hollow area 4 of determining part 5. As a result, detection sensitivity can be improved.

Additionally, acceptors 7 may be fixed on the surface of protrusion 70. When analyte 51 is present in sample 50, carrier 8 reacting with analyte 51 forms aggregate 16. If acceptors 7 are fixed on the surface of protrusion 70, aggregate 16 binds with acceptors on the surface of protrusion 70, and thus aggregate 16 cannot pass below protrusion 70. Accordingly, aggregates 16 cannot reach determining part 5. As a result, detection sensitivity can be improved.

Protrusion 70 may be formed integrally with supporting part 10. Integrated formation of protrusion 70 and supporting part 10 facilitates the manufacture.

Still more, the surface (bottom face) of protrusion 70 may be formed of metal layer 2. The manufacture becomes more simple if the surface is integrally formed with metal layer 2 of hollow area 4.

In FIGS. 8A and 8B, protrusion 70 protrudes to the passage from the upper side of optical sensor 200. However, protrusion 70 may protrude to the passage from the lower side of optical sensor 200. In this case, protrusion 70 may be formed integrally with supporting part 11. If narrowed area 20 is formed on the upper side of optical sensor 200, as is in this case, discharge area 12 is preferably formed on the lower side of optical sensor 200. By providing alternate passages before and after determining part 5 in this way, carriers 8 more likely stay in determining part 5. Or, protrusions 70 may be formed on the upper side and lower side of optical sensor 200 so that narrowed area 20 is connected to a center part of hollow area 4.

Furthermore, sample 50 and carrier 8 may be simultaneously input to the optical sensor from input part 6 without providing fixing part 9 in this exemplary embodiment. Also in this case, same effect is achieved. Accordingly, fixing part 9 is not indispensable in this exemplary embodiment. Even if fixing part 9 is not provided, input part 6 and hollow area 4 form a part of the passage where sample 50 flows from input part 6 to hollow area 4.

INDUSTRIAL APPLICABILITY

The optical sensor of the present invention has high detection sensitivity and a small and simple structure. Therefore, the optical sensor is applicable to small and low-cost biosensors or the like.

The invention claimed is:

1. An optical sensor comprising:
   a sensor body having a flow channel;
   an input opening provided on an upper side of the sensor body and configured to accept a sample into the flow channel;
   a fixing part provided in the flow channel and below the input opening and having a carrier fixed on the fixing part in such a manner that the carrier is released when the sample is applied on the fixing part via the input opening, the carrier having an acceptor that reacts with an analyte contained in the sample and is fixed on a surface of the carrier; and
   a determining part provided in the flow channel and configured to determine a presence of the analyte in the sample, the determining part including:
      a first support made of a glass or a plastic and being transparent to a visible light;
      a first metal layer disposed on an inner surface of the first support and configured to receive an electromagnetic wave, the first metal layer being capable of transmitting the visible light and having a thickness of 5 nm to 45 nm;
      a second metal layer facing the first metal layer, the second metal layer being capable of reflecting the visible light and having a thickness of 100 nm or more; and
      a hollow area sandwiched between the first metal layer and the second metal layer,
   wherein the input opening, the fixing part, and the hollow area form a part of the flow channel where the carrier and the sample flow from the fixing part to the hollow area, and
   the determining part is disposed laterally on downstream of the fixing part.

2. The optical sensor according to claim 1,
   wherein the carrier is fixed on the fixing part by physical adsorption.

3. The optical sensor according to claim 1,
   wherein the input opening is provided vertically above the fixing part.

4. The optical sensor according to claim 1, further comprising a discharge area connected to the hollow area of the determining part, and positioned downstream of the hollow area in the flow channel,
   wherein a length of the discharge area in a vertical direction is shorter than a length of the hollow area in a vertical direction.

5. The optical sensor according to claim 1, wherein the fixing part is lower than a bottom face of the hollow area.

6. The optical sensor according to claim 1, further comprising a protrusion provided upstream of the determining part in the flow channel, and protruding into the flow channel.

7. An optical sensor device comprising:
an optical sensor body including:
an input part configured to accept a sample into the sensor;
a determining part configured to determine a presence of an analyte in the sample, the determining part including:
a first metal layer configured to receive an electromagnetic wave;
a second metal layer facing the first metal layer; and
a hollow area sandwiched between the first metal layer and the second metal layer;
a first channel disposed between the input part and the determining part; and
a discharge area disposed on a downstream side of the determining part; and
a plurality of carriers configured to flow with the sample in the first channel, wherein:
each of the plurality of carriers is covered with acceptors,
the plurality of carriers are configured to form aggregates when the sample contains the analyte, a size of the aggregate being larger than a size of each of the plurality of carriers, and
a height of the first channel is smaller than the size of the aggregate and larger than the size of each of the plurality of carriers, and
the height of the discharge area is smaller than the height of the first channel.

8. The optical sensor device according to claim 7, wherein a protrusion is provided to make the height of the first channel to be smaller than the size of the aggregate and larger than the size of each of the carriers.

9. The optical sensor device according to claim 7, wherein a height of the discharge area is smaller than the size of each of the plurality of carriers, thereby preventing the plurality of carriers from flowing into the discharge area.

10. The optical sensor device according to claim 9, wherein:
the height of the discharge area is in a range from 350 nm to 750 nm.

11. The optical sensor according to claim 5, wherein a bottom face of the flow channel between the fixing part and the determining part is sloped.

12. The optical sensor according to claim 1, wherein the carrier is fixed on the fixing part by chemical bonding.

13. An optical sensor device comprising:
an optical sensor body including:
an input part configured to accept a sample into the sensor;
a determining part configured to determine a presence of an analyte in the sample, the determining part including:
a first metal layer configured to receive an electromagnetic wave;
a second metal layer facing the first metal layer; and
a hollow area sandwiched between the first metal layer and the second metal layer;
a first channel disposed between the input part and the determining part; and
a discharge area disposed on a downstream side of the determining part; and
a plurality of carriers configured to flow with the sample in the first channel, wherein:
each of the plurality of carriers is covered with acceptors,
the plurality of carriers are configured to form aggregates when the sample contains the analyte, a size of the aggregate being larger than a size of each of the plurality of carriers, and
a height of the first channel is smaller than twice a size of each of the plurality of carriers and larger than the size of each of the plurality of carriers, thereby preventing the aggregate from flowing into the determining part and allowing the plurality of carriers to flow into the determining part, and
the height of the discharge area is smaller than the height of the first channel.

14. The optical sensor device according to claim 13, further comprising:
a protrusion protruding into the first channel formed upstream side of the determining part,
wherein a distance between the protrusion and a face of the first channel is larger than the size of each of the plurality of carriers and smaller than twice the size of each of the plurality of carriers.

15. The optical sensor device according to claim 13, wherein a height of the discharge area is smaller than the size of each of the plurality of carriers, thereby preventing the plurality of carriers from flowing into the discharge area.

16. The optical sensor device according to claim 13, wherein a height of the first channel is configured to prevent the aggregate from flowing into the determining part and to allow the plurality of carriers to flow into the determining part.

17. The optical sensor device according to claim 16, wherein:
the height of the discharge area is in a range from 350 nm to 750 nm.

18. The optical sensor according to claim 1, wherein the fixing part is located just below the input opening with no element disposed between the input opening and the fixing part so that the sample applied from the input opening directly hits the fixing part.

19. The optical sensor device according to claim 7, wherein the optical sensor device is configured to detect presence of the analyte by detecting no color change, which is otherwise caused by the carrier, at the determining part.

20. The optical sensor device according to claim 13, wherein the optical sensor device is configured to detect presence of the analyte by detecting no color change, which is otherwise caused by the carrier, at the determining part.

21. The optical sensor according to claim 1, wherein the optical sensor has only one flow channel.

22. The optical sensor device according to claim 7, wherein the optical sensor device has only one flow channel.

23. The optical sensor device according to claim 13, wherein the optical sensor device has only one flow channel.

* * * * *